United States Patent
Cai et al.

(10) Patent No.: US 10,241,090 B2
(45) Date of Patent: Mar. 26, 2019

(54) METHOD AND APPARATUS FOR EVALUATING AN ULTRASONIC WELD JUNCTION

(71) Applicant: GM GLOBAL TECHNOLOGY OPERATIONS LLC, Detroit, MI (US)

(72) Inventors: Wayne W. Cai, Troy, MI (US); Debejyo Chakraborty, Novi, MI (US); Qian Lin, Troy, MI (US); John M. Moote, Plymouth, MI (US); Anthony Ottomano, Warren, MI (US); Teresa J. Rinker, Royal Oak, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 189 days.

(21) Appl. No.: 15/142,408

(22) Filed: Apr. 29, 2016

(65) Prior Publication Data
US 2017/0315100 A1 Nov. 2, 2017

(51) Int. Cl.
*G01N 29/44* (2006.01)
*G01N 3/08* (2006.01)
*G01N 29/04* (2006.01)
*G01N 29/34* (2006.01)
G01R 31/36 (2019.01)
B23K 20/10 (2006.01)
B23K 31/12 (2006.01)
B23K 101/38 (2006.01)

(52) U.S. Cl.
CPC .......... *G01N 29/4445* (2013.01); *G01N 3/08* (2013.01); *G01N 29/04* (2013.01); *G01N 29/045* (2013.01); *G01N 29/34* (2013.01); *B23K 20/10* (2013.01); *B23K 31/125* (2013.01); *B23K 2101/38* (2018.08); *G01N 2203/0073* (2013.01); *G01N 2291/025* (2013.01); *G01N 2291/0258* (2013.01); *G01R 31/3641* (2013.01)

(58) Field of Classification Search
CPC .. G01N 29/4445; G01N 29/045; G01N 29/34; G01N 3/08; G01N 29/04; G01N 2203/0073; G01N 2291/0258; G01N 2291/025; B23K 20/10; G01R 31/3641
See application file for complete search history.

(56) References Cited

U.S. PATENT DOCUMENTS

| | | | |
|---|---|---|---|
| 2014/0174184 A1* | 6/2014 | Furuya | G01N 3/32 73/577 |
| 2015/0147598 A1* | 5/2015 | Inoue | H01M 2/26 429/7 |
| 2015/0226634 A1* | 8/2015 | Matsuura | G01N 29/04 73/577 |
| 2017/0232660 A1* | 8/2017 | Raszillier | B29C 65/08 156/350 |

* cited by examiner

*Primary Examiner* — Xin Y Zhong
(74) *Attorney, Agent, or Firm* — Quinn IP Law

(57) ABSTRACT

A method and a test fixture for evaluating a battery cell composed of a cell body having a plurality of electrode foils, a positive terminal and a negative terminal, wherein the positive terminal and the negative terminal are each joined to the cell body at weld junctions. This includes retaining the cell body of the battery cell in a first clamping device. The terminal is grasped in a terminal gripper. A dynamic stress end effector coupled to the terminal gripper applies a vibrational excitation load to the terminal. A static stress end effector applies a static load to the terminal. Integrity of the weld junction is evaluated based upon the applied static load.

10 Claims, 3 Drawing Sheets

METHOD AND APPARATUS FOR EVALUATING AN ULTRASONIC WELD JUNCTION

TECHNICAL FIELD

The present disclosure relates to cells of a battery pack, and weld junctions thereof.

BACKGROUND

A battery pack typically includes multiple rechargeable battery cells that are connected in series or parallel to store and supply electric power to a distribution system. Each battery cell includes a plurality of electrode foils having alternately-placed positive and negative charge portions. The electrode foils are separated by separator material and enclosed within a sealed outer pouch that is filled with an electrolyte solution. The separator material, e.g., polyethylene and/or polypropylene film, helps prevent an electrical short condition while permitting the free transfer of electrical charge between electrode foils.

Positive and negative terminals each extend a short distance outside of the sealed pouch for each battery cell. The positive charge portions of the electrode foils are ultrasonically welded together and welded to the positive terminal, and the negative charge portions of the electrode foils are ultrasonically welded together and welded to the negative terminal. The ultrasonic welds are internal to and contained within the sealed outer pouch. Process capability of the ultrasonic welding process that forms the internal weld may be subject to variation due to ultrasonic welder variations and other factors.

SUMMARY

A method and a test fixture are provided for evaluating a battery cell composed of a cell body having a plurality of electrode foils, a positive terminal and a negative terminal, wherein the positive terminal and the negative terminal are each joined to the cell body at weld junctions. This includes retaining the cell body of the battery cell in a first clamping device. The terminal is grasped in a terminal gripper. A dynamic stress end effector coupled to the terminal gripper applies a vibrational excitation load to the terminal. A static stress end effector applies a static load to the terminal. Integrity of the weld junction is evaluated based upon the applied static load.

The above features and advantages, and other features and advantages, of the present teachings are readily apparent from the following detailed description of some of the best modes and other embodiments for carrying out the present teachings, as defined in the appended claims, when taken in connection with the accompanying drawings.

BRIEF DESCRIPTION OF THE DRAWINGS

One or more embodiments will now be described, by way of example, with reference to the accompanying drawings, in which.

DETAILED DESCRIPTION

Figure 1:
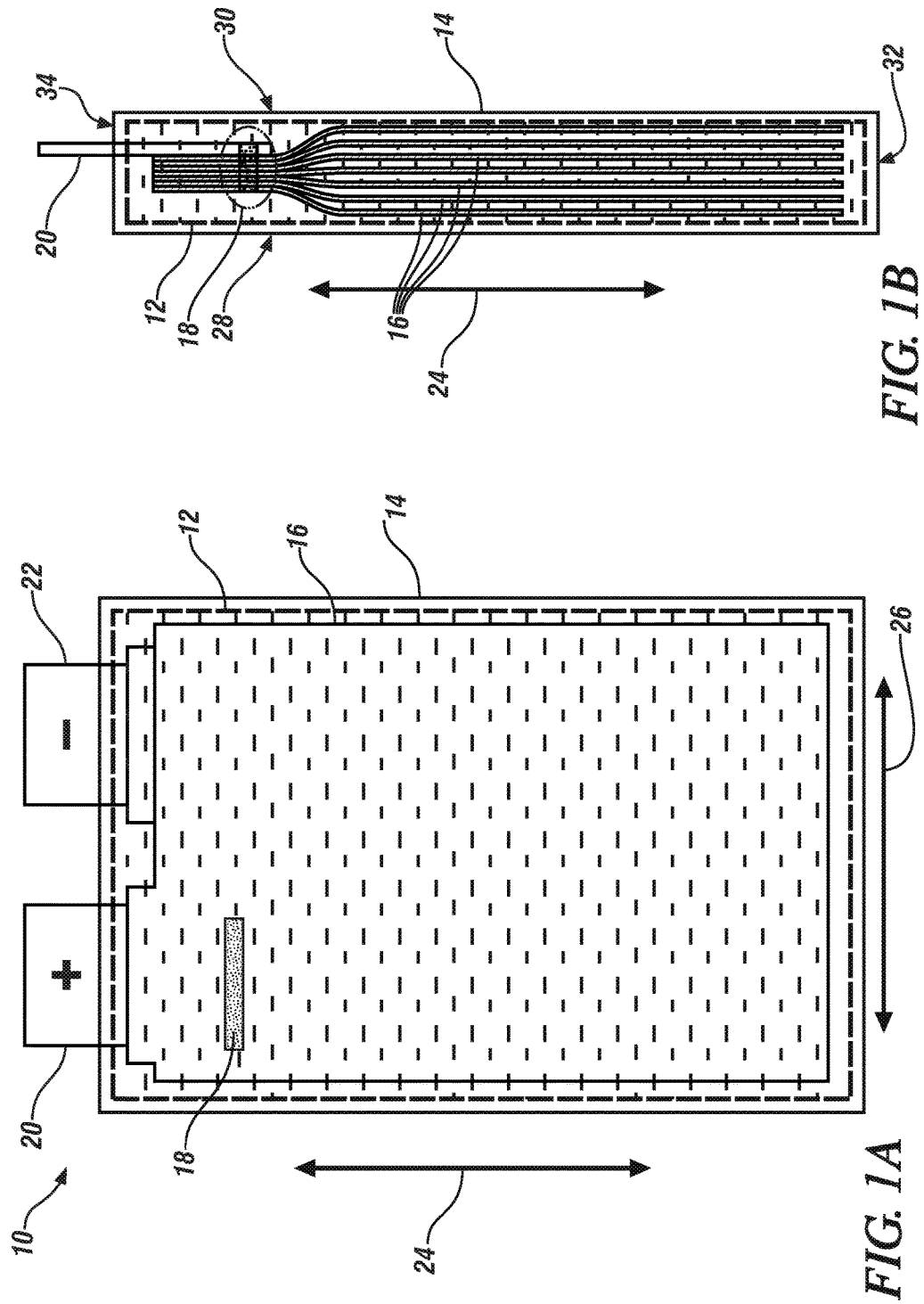
FIGS. 1A and 1B schematically illustrate a front view and a corresponding side view, respectively, of selected elements of a single battery cell, in accordance with the disclosure.

Referring now to the drawings, which are provided for the purpose of illustrating certain exemplary embodiments only and not for the purpose of limiting the same, FIGS. 1A and 1B schematically illustrate a front view and a corresponding side view, respectively, of selected elements of a single battery cell 10. Like numerals indicate like or corresponding parts throughout the several views. Those having ordinary skill in the art will recognize that terms such as "horizontal", "vertical", "above," "below," "upward," "downward," "top," "bottom," etc., are used descriptively for the figures, and do not represent limitations on the scope of the disclosure, as defined by the appended claims. The term "end effector" is defined as a device that may be controlled to accomplish a pre-defined task in response to a control command, and may be mechanically actuated, electro-mechanically actuated, pneumatically actuated, or may employ another actuation system.

The battery cell 10 includes a cell body 14 that includes a plurality of electrode foils 16 in plate form that are arranged in a vertical stack and contained within a sealed pouch 12 that is filled with electrolytic fluid in one embodiment. Negative charge portions of the plurality of electrode foils 16 are ultrasonically welded together and welded to a negative terminal 22, preferably employing ultrasonic welding methods. Similarly, positive charge portions of the electrode foils 16 are ultrasonically welded together and welded to the positive terminal 20. A weld junction 18 joins the electrode foils 16 and the positive terminal 20, and is preferably formed parallel to a lateral axis 26, although the concepts described herein are not so limited. The weld junction 18 between the electrode foils 16 and the positive terminal 20 may be in the form of a lap weld junction, although the concepts described herein are not so limited. A second weld junction (not shown) joins the negative charge portions of the electrode foils 16 and the negative terminal 22. The battery cell 10 may be nominally described in terms of a first face portion 28, a second face portion 30, a bottom portion 32 and a top portion 34. The lateral axis 26 extends in a horizontal direction, as shown, between the first face portion 28 and the second face portion 30. A longitudinal axis 24 extends between the bottom portion 32 and the top portion 34 in a vertical direction as shown and orthogonal to the lateral axis 26. Other details related to the battery cell 10 are known to one of ordinary skill in the art. In one embodiment, the single battery cell 10 is a lithium-ion battery cell that is rechargeable, although the concepts described herein may be applied to other battery cell configurations that are fabricated in a manner described herein. Alternatively, the battery cell 10 may be configured as a cylindrical device having terminals extending from one of its ends. Alternatively, the battery cell 10 may be configured as a brick-shaped device having terminals extending from one of its ends. The concepts described herein apply to any configuration of the battery cell 10.

Figure 2:
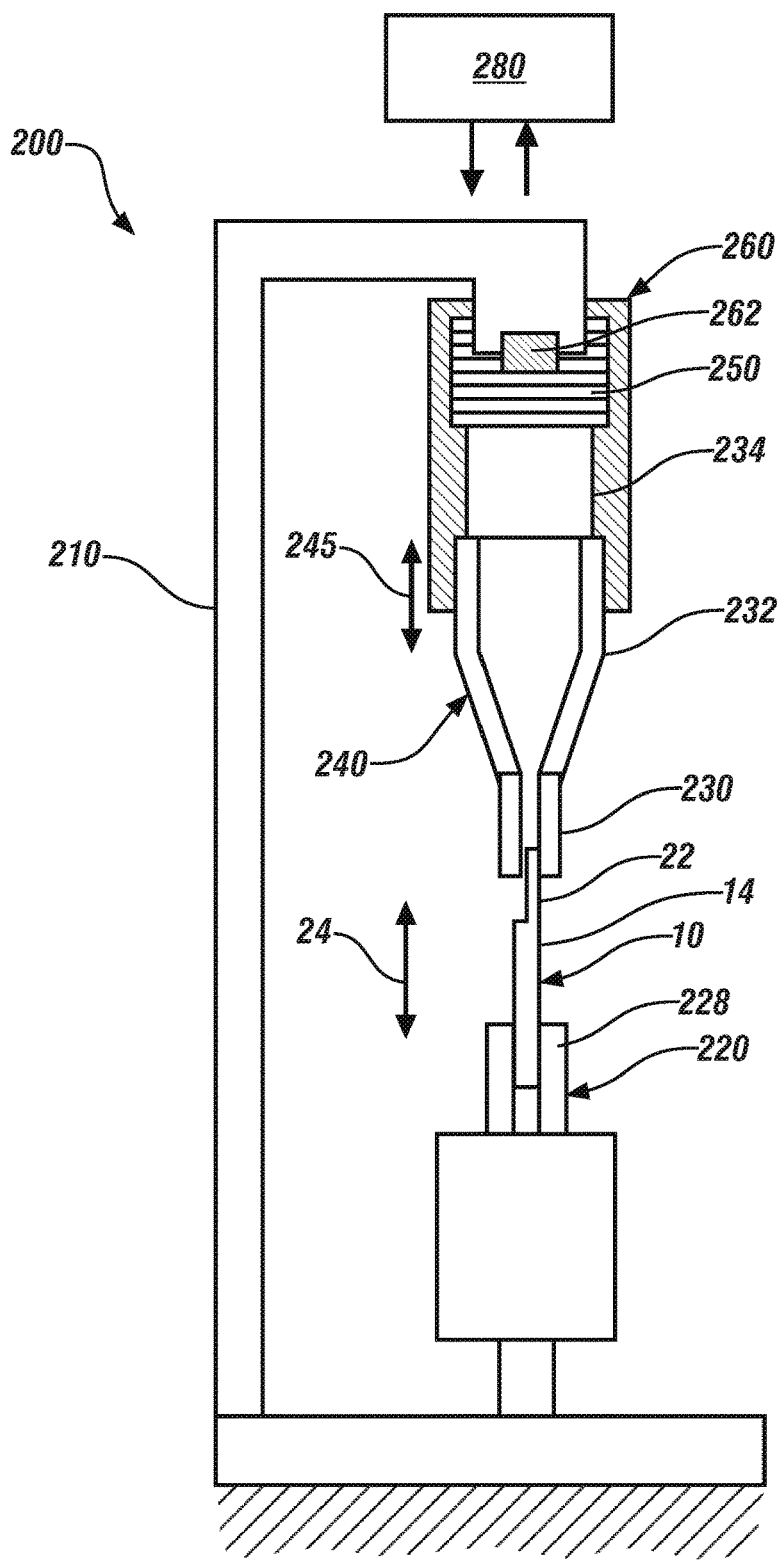
FIG. 2 schematically shows a test fixture for evaluating a workpiece, including a first clamping device, a dynamic stress end effector, a static stress end effector, and a controller, in accordance with the disclosure.

FIG. 2 schematically shows a test fixture 200 for evaluating a workpiece, wherein the workpiece is an embodiment of the battery cell 10 described with reference to FIGS. 1A and 1B. As shown, the battery cell 10 includes the negative terminal 22 and cell body 14. The test fixture 200 includes a frame 210, a first clamping device 220, a dynamic stress end effector 240, a static stress end effector 260, and a controller 280. The test fixture 200 is disposed to apply vibrational excitation loads and static loads to the positive and negative terminals 20, 22 of an embodiment of the battery cell 10.

The first clamping device 220 includes a gripping device 228 that is configured to retain a workpiece, which includes the cell body 14 of the battery cell 10 in one embodiment. The first clamping device 220 and gripping device 228 may be configured as a force-closure clamping device that exerts a normal force on the cell body 14 to effect its retention in one embodiment. Alternatively, the first clamping device 220 may be configured as a form-closure clamping device that accommodates geometric features of the cell body 14 of the battery cell 10 to effect its retention. Alternatively, the first clamping device 220 may be a combination of the force-closure clamping device and a form-closure clamping device. As shown, the first clamping device 220 and gripping device 228 are configured as a force-closure device, which may include a first plate section arranged in parallel with an opposed second plate section in one embodiment, wherein the first and second plate sections may be urged together to apply a gripping force on the cell body 14 of the battery cell 10. The relevant dimensions of the first clamping device 220 are preferably selected to accommodate dimensions of a specific embodiment of the cell body 14 of the battery cell 10. The gripping device 228 is disposed to impose a clamping force on the cell body 14 when the battery cell 10 is inserted into the clamping device 220. The gripping device 228 may be any suitable force or pressure activated device, such as a pneumatically-powered cylinder having two-way control capability to apply and remove the clamping force. The applied clamping force mechanically retains the inserted battery cell 10 for purposes of performing dynamic and static testing on the battery cell 10, as described herein. The removal of the clamping force urges the first plate section away from the second plate section to permit removal of the inserted battery cell 10. Details related to clamping mechanisms for test fixtures are known to one of ordinary skill in the art, and thus not described in further detail.

The dynamic stress end effector 240 includes a terminal gripper 230 that is mechanically coupled to a dynamic stress mechanism 250 via a waveguide device 232 and a force coupler 234. The terminal gripper 230 is preferably located adjacently above the first clamping device 220 (as shown), thus permitting it to interact with and mechanically grip one of the positive and negative terminals 20, 22 of the battery cell 10 when inserted into the first clamping device 220. The dynamic stress mechanism 250 is a repetitive stress-applying device that generates a vibrational excitation load that is transferred through the waveguide 232, the force coupler 234, and the terminal gripper 230 to the one of the positive and negative terminals 20, 22 of the battery cell 10 that is gripped. The dynamic stress mechanism 250 is a piezoelectric device that is capable of generating high frequency vibration that is propagated through the force coupler 234 and the waveguide 232 to the terminal gripper 230. The vibrational excitation load is preferably applied in a direction that is parallel to the longitudinal axis of the battery cell 10 as indicated by arrow 245. The vibrational excitation load may be in the in the form of an ultrasonic vibrational load. In one embodiment, the ultrasonic vibrational load includes an oscillatory motion that is applied at a frequency that is within a range between 10 kHz and 100 kHz, at an amplitude that is preferably within a range between several micrometers and one hundred micrometers, for a duration of time between 0.5 s and 10 s. Other suitable vibrational excitation loads that are described in terms of vibrational frequencies, amplitudes and durations may be selected, depending upon the particular design of the embodiment of the battery cell 10, with a process for such selection known to one of ordinary skill in the art.

The static stress end effector 260 is preferably co-located with the dynamic stress end effector 240 in the test fixture 200, which allows it to employ the terminal gripper 230. The static stress end effector 260 includes a mechanical load applicator that preferably includes a load cell 262 including a linear measurement system. Load cells and associated linear measurement systems are known to one of ordinary skill in the art, and thus not described in detail herein. The static stress end effector 260 is configured to apply a preset static mechanical load in the form of a tensile load on one of the positive and negative terminals 20, 22 of the battery cell 10 in relation to the cell body 14 and the plurality of electrode foils 16, wherein the static mechanical load is propagated through the respective terminal 20, 22 to the plurality of electrode foils 16 through the weld junction 18. The magnitude of the preset static mechanical load is less than an elastic limit or a yield point for the weld junction 18 when the weld junction 18 has been formed in accordance with welding specifications, and may be empirically determined. The linear measurement system of the load cell 262 monitors a displacement between the first clamping device 220 and the terminal gripper 230, and is associated with the one of the positive and negative terminals 20, 22 of the battery cell 10 in relation to the plurality of electrode foils 16. Details associated with the load cell 262 including the linear measurement system are known to one of ordinary skill in the art. The controller 280 communicates with the first clamping device 220, the dynamic stress end effector 240 and the static stress end effector 260 to monitor various sensors and generate control commands for various actuators to accomplish predetermined tasks. The static stress end effector 260 is shown collocated with the dynamic stress end effector 240 in the test fixture 200, although the concepts described herein are not so limited. One skilled in the art appreciates that the dynamic stress end effector 240 may be collocated with the static stress end effector 260, or separately located, depending upon numerous factors.

The terms controller, control module, module, control, control unit, processor and similar terms refer to any one or various combinations of Application Specific Integrated Circuit(s) (ASIC), electronic circuit(s), central processing unit(s), e.g., microprocessor(s) and associated non-transitory memory component in the form of memory and storage devices (read only, programmable read only, random access, hard drive, etc.). The non-transitory memory component is capable of storing machine readable instructions in the form of one or more software or firmware programs or routines, combinational logic circuit(s), input/output circuit(s) and devices, signal conditioning and buffer circuitry and other components that can be accessed by one or more processors to provide a described functionality. Input/output circuit(s) and devices include analog/digital converters and related devices that monitor inputs from sensors, with such inputs monitored at a preset sampling frequency or in response to a triggering event. Software, firmware, programs, instructions, control routines, code, algorithms and similar terms mean any controller-executable instruction sets including calibrations and look-up tables. Each controller executes control routine(s) to provide desired functions, including monitoring inputs from sensing devices and other networked controllers and executing control and diagnostic instructions to control operation of actuators. Routines may be executed at regular intervals, or in response to occurrence of a triggering event. Communication between controllers, and communication between controllers, actuators and/or sensors may be accomplished using a direct wired point-to-point link, a networked communication bus link, a wireless link or any other suitable communication link. Communication includes exchanging data signals in any suitable form, including, for example, electrical signals via a conductive medium, electromagnetic signals via air, optical signals via optical waveguides, and the like. The data signals may include discrete, analog or digitized analog signals representing inputs from sensors, actuator commands, and communication between controllers. The term "signal" refers to any physically discernible indicator that conveys information, and may be any suitable waveform (e.g., electrical, optical, magnetic, mechanical or electromagnetic), such as DC, AC, sinusoidal-wave, triangular-wave, square-wave, vibration, and the like, that is capable of traveling through a medium.

Figure 4:
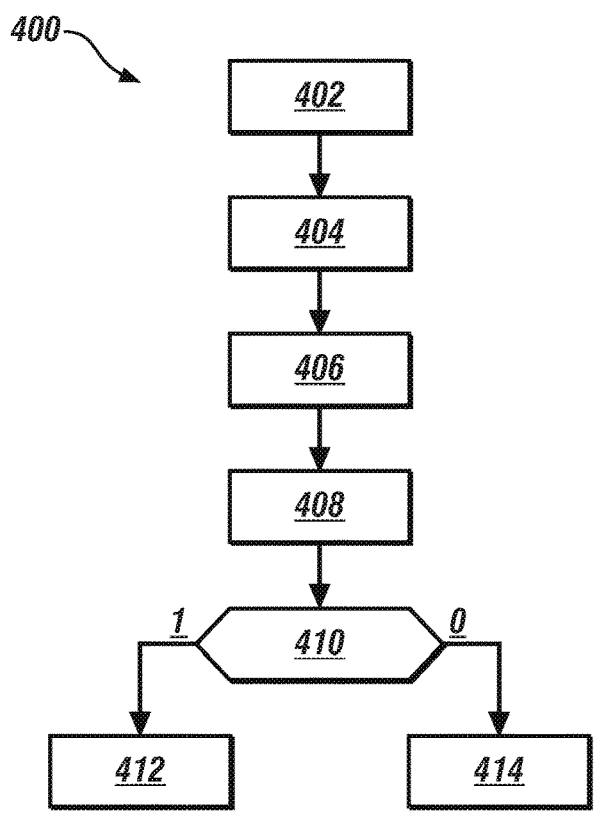
FIG. 4 schematically shows a stress test routine that may be executed in a controller to employ the test fixture to non-destructively evaluate a workpiece in the form of the battery cell described with reference to FIGS. 1A and 1B, in accordance with the disclosure.

FIG. 4 schematically shows in flowchart form a stress test routine 400 that may be executed in the controller 280 to employ the test fixture 200 to non-destructively evaluate a workpiece in the form of the battery cell 10 described with reference to FIGS. 1A and 1B. More specifically, the stress test routine 400 may be advantageously applied to evaluate the weld junction 18 between one of the terminals 20, 22 and the plurality of electrode foils 16 on the battery cell 10. Table 1 is provided as a key wherein the numerically labeled blocks and the corresponding functions are set forth as follows, corresponding to the stress test routine 400. Those having ordinary skill in the art will recognize that the teachings may be described herein in terms of functional and/or logical block components and/or various processing steps. It should be realized that such block components may be composed of any number of hardware, software, and/or firmware components configured to perform the specified functions.

TABLE 1

| BLOCK | BLOCK CONTENTS |
|---|---|
| 402 | Insert workpiece into the first clamping device of the test fixture, retain the workpiece with the first clamping device, and clamp the terminal of the workpiece with the terminal gripper |
| 404 | Apply pre-tension to the terminal |
| 406 | Operate the dynamic stress end effector |
| 408 | Operate the static stress end effector |
| 410 | Evaluate integrity of the weld junction of the workpiece |
| 412 | Indicate workpiece is acceptable |
| 414 | Indicate workpiece is unacceptable |

Figure 3:
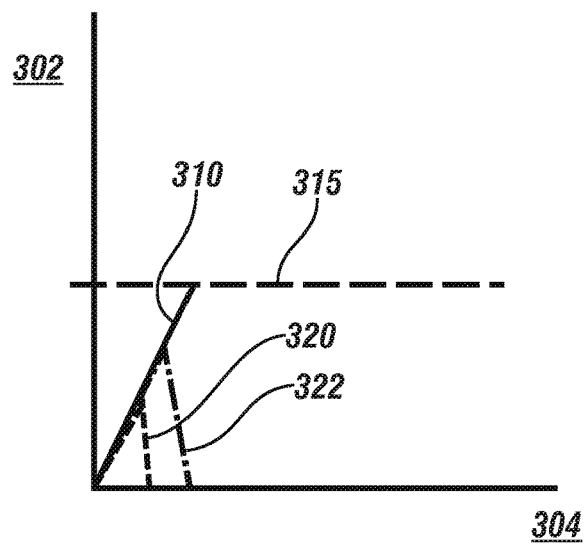
FIG. 3 graphically illustrates a load/displacement diagram indicating possible results associated with executing a static load test on an embodiment of the battery cell that is described with reference to FIGS. 1A and 1B, in accordance with the disclosure.

Execution of the stress test routine 400 may proceed as follows. The steps of the stress test routine 400 may be executed in any suitable order, and are not limited to the order described with reference to FIG. 4. As indicated, the stress test routine 400 includes inserting a workpiece in the form of an embodiment of the battery cell 10 into the first clamping device 220 of the test fixture 200. The cell body 14 of the battery cell 10 is clamped or otherwise retained by the first clamping device 220, and one of the positive and negative terminals 20, 22 of the battery cell 10 is clamped by the terminal gripper 230 of the dynamic stress end effector 240 (402). A pre-tension load is applied to the one of the terminals 20, 22 by the state stress end effector 260 to remove any slack between the one of the terminals 20, 22 and the cell body 14 (404). Once the clamping is complete and any residual slack is removed, the dynamic stress end effector 240 is operated to apply a repetitive stress by applying ultrasonic vibration at the one of the positive and negative terminals 20, 22 of the battery cell 10. The purpose of applying ultrasonic vibration at the one of the positive and negative terminals 20, 22 of the battery cell 10 is to apply stress to the weld junction 18 of the battery cell 10. The applied stress serves to weaken a poorly executed weld junction 18, and thus increase the likelihood that an unacceptable weld junction is identified before further processing of the battery cell 10. The ultrasonic vibration is applied in a direction that is parallel to the longitudinal axis 24 of the battery cell 10, and is in the form of a repetitively-executed linear oscillatory motion that is applied at a frequency that is within a range between 10 kHz and 100 kHz, at an amplitude that is preferably within a range between several micrometers and one hundred micrometers, for a duration of time between 0.5 s and 10 s (406). The static stress end effector 260 is operated to apply a static load between the selected terminal 20, 22 and the cell body 14 while monitoring displacement (408). In one embodiment, the ultrasonic vibration is applied simultaneously with the static load. The monitored displacement is employed to evaluate integrity of the weld junction 18 based upon the applied static load or the applied static load in conjunction with the ultrasonic vibration (410). FIG. 3 graphically illustrates one embodiment of load/displacement diagram that may be associated with the stress test routine 400. When the monitored displacement (410) indicates that the one of the terminals 20, 22 of the battery cell 10 has passed the static load test, i.e., the integrity of the weld junction 18 has been verified (1), the tested one of the terminals 20, 22 of the battery cell 10 is identified as acceptable (412). The process described with reference to steps 402 through 412 is repeated for the other one of the terminals 20, 22. When the monitored displacement (410) of the displacement indicates that the battery cell 10 has not passed the static load test, i.e., the integrity of the weld junction 18 for one of the terminals 20, 22 has been compromised (0), the battery cell 10 is identified as an unacceptable part and rejected (414). When the integrities of the weld junctions associated with both of the terminals 20, 22 are verified, or one of the weld junctions associated with one of the terminals 20, 22 has been identified as being unacceptable, the workpiece is removed from the test fixture 200. Compromised integrity of a weld junction may include a weld fracture, a tearing of material in the area of the weld junction, or another fault. Such weld junction faults are known to one of ordinary skill in the art.

FIG. 3 graphically illustrates a load/displacement diagram indicating possible results associated with executing a static load test on an embodiment of the battery cell 10 that is described with reference to FIGS. 1A and 1B. Static load 302 is indicated on the vertical axis in relation to displacement 304, which is shown on the horizontal axis. Line 315 indicates a maximum magnitude for the preset static mechanical load that is less than an elastic limit or a yield point for the weld junction 18 of a sample of the battery cell 10 when the weld junction 18 has been formed in accordance with welding specifications. Line 310 indicates a first load/ displacement curve, which is related to results of a test of a sample of the battery cell 10 that has been subjected to the stress test routine described with reference to FIG. 4 and passed, i.e., the integrity of the weld junction 18 has been maintained. The first load/displacement curve shown with reference to Line 310 indicates that the weld junction 18 of the sample of the battery cell 10 has been able to withstand the applied static load up to the maximum magnitude 315 for the preset static mechanical load after the ultrasonic vibration has been applied in a direction that is parallel to the longitudinal axis of the battery cell 10. Lines 320 and 322 indicate load/displacement curves that are related to results of tests of samples of the battery cell 10 that have been subjected to the stress test routine described with reference to FIG. 4 and have not passed. The load/displacement curves shown with reference to Line 320 and 322 indicate that the weld junction 18 of the samples of the battery cell 10 were not able to withstand the applied static load up to the maximum magnitude 315 for the preset static mechanical load after the ultrasonic vibration has been applied to the respective terminal 20, 22 in a direction that is parallel to the longitudinal axis of the sample of the battery cell 10. The load/displacement results shown with reference to FIG. 3 provide one embodiment of results from a static load test.

The flowchart illustrates the architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

The invention claimed is:

1. A method for evaluating a battery cell composed of a cell body having a plurality of electrode foils, a positive terminal and a negative terminal, wherein the positive terminal and the negative terminal are each joined to the cell body at weld junctions, the method comprising:
    retaining the cell body of the battery cell in a first clamping device;
    clamping one of the positive and negative terminals in a terminal gripper;
    applying, employing a dynamic stress end effector coupled to the terminal gripper, a vibrational excitation load to the clamped one of the positive and negative terminals;
    applying a static load to the clamped one of the positive and negative terminals; and
    evaluating integrity of the weld junction of the clamped one of the positive and negative terminals based upon the applied static load.

2. The method of claim 1, wherein applying the vibrational excitation load to the clamped one of the positive and negative terminals comprises applying an ultrasonic vibrational load to the terminal.

3. The method of claim 2, wherein the ultrasonic vibrational load is applied to the clamped one of the positive and negative terminals in a direction that is parallel to the longitudinal axis of the battery cell.

4. The method of claim 2, wherein the ultrasonic vibrational load comprises an oscillatory motion that is applied at a frequency that is within a range between 10 kHz and 100 kHz.

5. The method of claim 2, wherein the ultrasonic vibrational load comprises a repetitively-executed linear oscillatory motion that is applied at an amplitude that is within a range between several micrometers and one hundred micrometers.

6. The method of claim 2, wherein the ultrasonic vibrational load comprises an oscillatory motion that is applied for a duration of time between 0.5 s and 10 s.

7. The method of claim 1, wherein applying a static load to the clamped one of the positive and negative terminals comprises applying a preset static tensile load between the terminal and the cell body, wherein the static load is propagated through the terminal to the electrode foils through the weld junction.

8. The method of claim 1, wherein evaluating integrity of the weld junction based upon the applied static load comprises monitoring displacement of the clamped one of the positive and negative terminals in relation to the battery cell.

9. The method of claim 1, comprising applying the static load to the clamped one of the positive and negative terminals simultaneously with applying the vibrational excitation load to the clamped one of the positive and negative terminals.

10. A method for evaluating a weld junction disposed to mechanically join a terminal to a plurality of electrode foils of a battery cell, the method comprising:
    retaining the battery cell in a first clamping device;
    clamping the terminal in a terminal gripper;
    applying, employing a dynamic stress end effector coupled to the terminal gripper, an ultrasonic vibrational load to the terminal via the terminal gripper; and then
    applying, employing a static stress end effector, a static load to the terminal via the terminal gripper; and
    evaluating integrity of the weld junction based upon the applied static load.

* * * * *